(12) United States Patent
Porzelt

(10) Patent No.: US 9,785,808 B2
(45) Date of Patent: Oct. 10, 2017

(54) CONTROL DEVICE, MEDICAL CONTROL SYSTEM AND METHOD FOR TRANSMITTING A COMMAND

(71) Applicant: Klaus Porzelt, Nuremberg (DE)

(72) Inventor: Klaus Porzelt, Nuremberg (DE)

(73) Assignee: Siemens Aktiengesellschaft, München (DE)

(*) Notice: Subject to any disclaimer, the term of this patent is extended or adjusted under 35 U.S.C. 154(b) by 25 days.

(21) Appl. No.: 14/605,471

(22) Filed: Jan. 26, 2015

(65) Prior Publication Data

US 2015/0220763 A1   Aug. 6, 2015

(30) Foreign Application Priority Data

Feb. 4, 2014 (DE) .................. 10 2014 201 931

(51) Int. Cl.
*A61B 6/10* (2006.01)
*G06K 7/10* (2006.01)
*G08C 17/00* (2006.01)
*A61B 6/00* (2006.01)

(52) U.S. Cl.
CPC ............ *G06K 7/10366* (2013.01); *A61B 6/10* (2013.01); *G06K 7/10158* (2013.01); *G08C 17/00* (2013.01); *A61B 6/00* (2013.01)

(58) Field of Classification Search
CPC .................................. A61B 6/00; A61B 6/10
See application file for complete search history.

(56) References Cited

U.S. PATENT DOCUMENTS

| 7,911,348 B2 | 3/2011 | Rodgers |
| 2004/0160323 A1* | 8/2004 | Stilp ............. G08B 3/1083 340/572.1 |
| 2006/0165371 A1 | 7/2006 | Zwart |
| 2006/0232275 A1 | 10/2006 | Leussler |

(Continued)

FOREIGN PATENT DOCUMENTS

| CN | 1689056 A | 10/2005 |
| CN | 202600740 U | 12/2012 |

(Continued)

OTHER PUBLICATIONS

Korean office Action for related Korean Application No. 10 2015 0014900 dated Feb. 2, 2016, with English Translation.

(Continued)

*Primary Examiner* — Benyam Haile
(74) *Attorney, Agent, or Firm* — Lempia Summerfield Katz LLC

(57) ABSTRACT

The embodiments relate to a control device for transmission of at least one command. The control device includes at least one RFID transponder unit for transmission of an identification code and a read device for reading out the identification code of the RFID transponder unit. The RFID transponder unit is disposed within a medical device and has at least one initiation device for initiating the at least one command. In one embodiment, the control device includes three alarm units for triggering different alarms, such as after initiation of the at least one command, after interruption of a transmission link, and after a charging value of an energy storage unit has fallen below a threshold value.

23 Claims, 2 Drawing Sheets

(56) References Cited

U.S. PATENT DOCUMENTS

| | | | |
|---|---|---|---|
| 2007/0194100 A1* | 8/2007 | Plassky | G06K 19/0704 235/375 |
| 2007/0257800 A1* | 11/2007 | Yang | A61N 1/08 340/572.7 |
| 2010/0102964 A1* | 4/2010 | Steer | G06Q 10/0833 340/572.1 |
| 2010/0141430 A1* | 6/2010 | Steer | G01S 19/17 340/539.13 |
| 2010/0262139 A1 | 10/2010 | Beller et al. | |
| 2012/0196661 A1* | 8/2012 | Snoddy | A63F 9/0612 463/9 |
| 2013/0109965 A1* | 5/2013 | Assman | A61M 5/484 600/431 |
| 2014/0275970 A1* | 9/2014 | Brown | G01R 33/3692 600/413 |
| 2015/0108210 A1* | 4/2015 | Zhou | H03H 7/18 235/375 |
| 2015/0221194 A1* | 8/2015 | Sarkar | G08B 13/2465 340/870.16 |

FOREIGN PATENT DOCUMENTS

| | | |
|---|---|---|
| DE | 19752278 A1 | 6/1999 |
| DE | 102007060810 A1 | 6/2009 |
| DE | 102011085597 A1 | 5/2013 |
| JP | 2007502138 A | 2/2007 |
| JP | 2011505929 A | 3/2011 |
| KR | 20100036697 A | 4/2010 |

OTHER PUBLICATIONS

German Office Action dated Sep. 30, 2014 for corresponding German Patent Application No. DE 10 2014 201 931.1 with English translation.

"Das schnurlose digitale DECT-Telefon für bis zu 6 Mobilteile"; Siemens AG; 2010.

Chinese Office Action for related Chinese Application No. 2015 100 326 90.3 dated May 3, 2017 with English Translation.

\* cited by examiner

CONTROL DEVICE, MEDICAL CONTROL SYSTEM AND METHOD FOR TRANSMITTING A COMMAND

CROSS-REFERENCE TO RELATED APPLICATIONS

This application claims the benefit of DE 10 2014 201 931.1, filed on Feb. 4, 2014, which is hereby incorporated by reference in its entirety.

TECHNICAL FIELD

The present embodiments relate to a control device for transmitting at least one command, a medical control system with such a control device, a method for transmitting at least one command between an RFID transponder unit and a read device and also a corresponding RFID transponder unit and a read device.

BACKGROUND

The transmission of commands by control devices, as well as by corresponding medical control systems, is a widespread area of activity, such as in the clinical field.

In the everyday clinical environment, an explicit transmission of a plurality of commands, such as for an efficient and targeted monitoring or activation of medical devices, may represent a complex challenge.

SUMMARY AND DESCRIPTION

The scope of the present invention is defined solely by the appended claims and is not affected to any degree by the statements within this summary. The present embodiments may obviate one or more of the drawbacks or limitations in the related art.

The object of the embodiments is to specify a control device that makes it possible to transmit at least one command and with which an efficient triggering of an alarm is also possible.

In such cases, a control device is provided for transmitting at least one command, including (1) at least one RFID transponder unit for transmission of an identification code and (2) a read device for reading out the identification code of the RFID transponder unit, wherein the RFID transponder unit is disposed within a medical device and has at least one initiating device for initiating the at least one command.

An RFID transponder unit and a read device together form an RFID system. The RFID transponder unit contains an identification code that the read device may read out. Coupling occurs through the magnetic alternating fields created by the read device or through high-frequency radio waves that are sent out by the read device and thereby make wireless or cableless communication possible.

A medical device, (e.g., a medical imaging device), is a device for detecting, processing, evaluating, and/or storing image information in the form of image data. To detect the image information, acoustic methods such as ultrasound (US), emission methods such as emission computed tomography (ECT), and positron emission tomography (PET), optical methods, radiological methods such as x-ray tomography and computed tomography (CT) may be used. The detection may also be undertaken by magnetic resonance tomography (MR or MRT) or by combined methods. The medical imaging device may deliver 2-dimensional (2D) or multidimensional, such as 3-dimensional (3D) or 4-dimensional (4D) picture data, which may be stored and/or processed in different formats. The medical imaging device may be used in diagnostics, for example in medical diagnostics.

An initiation device is, for example, a push-button, a key, or a knob for initiating the at least one command. The initiation device may be operated manually by a user, (e.g., by a patient).

A command is to be understood, for example, as a modification of a parameter, such as the modification of the volume of music, of the volume of speech, of illumination or of ventilation, but also the triggering of an alarm, for example. The initiation device is then configured to initiate the corresponding command.

The embodiments use the arrangement of RFID transponder unit and read device to provide at least one command to be initiated by the initiation device of the RFID transponder unit. This provides a notification to medical operating personnel to be initiated.

In one embodiment, the control device includes a first alarm unit configured to trigger a first alarm after initiation of the at least one command. In this case, a first alarm is to be understood, for example, as an alarm of a patient who may trigger the alarm within the medical device. The alarm may be signaled, for example, by flashing of the first alarm unit at the read device. This provides the patient with the opportunity of drawing attention to himself or herself if the patient becomes lightheaded or wishes to make contact for some other reason.

In one embodiment, the control device is configured for switching off and/or restarting an activation mode of the first alarm. In this case, activation mode is to be understood as a mode that makes active triggering of the alarm possible. An alarm is to be understood, for example, as the sending of a specific command and/or data pattern. The alarm may also be realized by illumination and/or flashing of a diode and/or an output of an acoustic signal. This enhances operating convenience for medical operating personnel, for example, since the sending of an alarm, for example, for patients who are continuously triggering the alarm, does not necessarily have to occur continuously. Thus, by restarting the activation mode, for example, the triggering of the first alarm may be suppressed for a specific time. The embodiment for switching off the activation mode also includes switching off during the sending of a first alarm, if the alarm has already been noted for example and is no longer to be transmitted.

In a further form of embodiment, the control device includes a user interface by which the switching off and/or restarting of the activation mode of the first alarm is able to be carried out. In this case, the user interface may be configured as a switch, knob, or lever, (e.g., in the read device). The activation mode is thus able to be switched off or restarted in a simple manner.

In one embodiment, the control device is configured for transmission of at least two commands and the RFID transponder unit has at least two initiation devices for initiating at least two commands. Through the at least two initiation devices, (configured, for example, as pushbuttons, keys, or knobs), further commands or parameters able to be selected by the patient may be transmitted. Thus, for example, a number of modifications may also be notified or transferred simultaneously.

In one embodiment, the control device includes a first monitoring unit configured for monitoring a transmission link between the RFID transponder unit and the read device. In this case, the monitoring unit may detect whether the transmission link is interrupted. Thus, for example, accidentally moving the RFID transponder unit out of range of the read device is able to be noticed and is thus also able to be rectified especially quickly. The monitoring unit may be disposed at the read device.

In one embodiment, the RFID transponder unit includes a command generation unit configured for transmission of a further command that is initiated independently of the initiation device 106. The transmission of the further command may include, for example, of continuously sending a status message such as "RFID detected" or a specific data pattern and signals the correct functioning of the system. The transmission link may also be monitored with the command.

In a further form of embodiment, the RFID transponder unit is configured for a continuous transmission of the further command. Thus, a status message, such as "RFID detected," for example, may be sent continuously at a specific interval. This enables the transmission link to be monitored in a reliable manner.

In one embodiment, the control device includes a second alarm unit configured to trigger a second alarm if the transmission link is interrupted. An alarm is to be understood, for example, as the sending of a specific command and/or data pattern, but the alarm may also be realized by the illumination and/or flashing of a diode and/or by an output of an acoustic signal. This provides the interruption to be identified in good time and correctly-functioning transmission to be guaranteed. Advantageously, the second alarm is triggered after the interruption has exceeded a certain period of time. In such cases, the interruption may be detected, for example, by the absence of the status message "RFID detected." The second alarm may be signaled at the read device in this case.

In one embodiment, the RFID transponder unit includes a memory unit configured for storing the at least one initiated command. Thus, the initiated command may still be stored in the event of an interruption of the transmission link. This command may then be notified again after restoration of a correctly functioning transmission link. Thus no information about an initiated command is lost.

In one embodiment, the RFID transponder unit is configured for continuously sending at least one initiated command. It may thus be insured that the initiated command is sent for longer than a time limit for a transmission outage. This results in additional monitoring and a higher reliability of the facility.

In a further form of embodiment, the control device includes a second monitoring unit configured for monitoring a power supply of the RFID transponder unit. Monitoring of the power supply of the RFID transponder unit additionally supports reliable operation of the unit.

In one embodiment, the RFID transponder unit includes an energy storage unit and the control device includes a third alarm unit configured to trigger a third alarm if a charge value of the energy storage unit falls below a threshold. A third alarm is to be understood, for example, as the sending of a specific command and/or data pattern. The alarm may also be realized by illumination and/or flashing of a diode and/or by an output of an acoustic signal. An energy storage unit is to be understood as a battery, for example. The third alarm is triggered as soon as the charging value of the battery falls below the threshold, e.g., becomes smaller for example than a percentage of a maximum charge of the battery. The charging value of the energy storage unit may thus be reliably monitored and a complete discharge of the energy storage unit prevented. Continuous operation of the RFID transponder unit is thus guaranteed.

In one embodiment, the RFID transponder unit is programmable. In this case, a programmable RFID transponder unit is to be understood as a transponder unit with which a bidirectional data link may be set up, e.g., a data link with which a response to an RFID transponder unit may be set up. Thus, a specific behavior, such as illumination, flashing, vibration or buzzing of the RFID transponder unit may be defined by different programmed data patterns. In this way, for example, a response may be given to a patient who is located within the medical device.

In one embodiment, the read device of the control device is configured for sending on a whole-number multiple of a predeterminable basic frequency. In this case, a basic frequency is to be understood as a frequency that is predetermined by the medical device, for example, a frequency that corresponds to a system clock of a magnetic resonance device. By the read device sending on a whole-number multiple of this predeterminable basic frequency, the medical device will not be disturbed.

In a further form of embodiment, the read device of the control device is configured for sending with a frequency that is greater than a predeterminable limit frequency. If the read device sends with a frequency that is greater than a predeterminable limit frequency, for example, a highest frequency of a medical device, the medical device will also not be disturbed by this.

In one embodiment, the control device includes a filter unit configured for filtering an output signal of the read device. In this case, a filter unit is to be understood as a heavily-attenuating bandpass or highpass, so that measurements of a medical device, such as of a medical resonance device, will not be influenced.

In one embodiment, the read device includes at least two antennas. A higher range of the RFID transponder unit is achieved by this.

In one embodiment, the control device includes a transfer unit configured for a transfer of the at least one command from the read device to the medical device. This enables the command to be further processed in the control device and/or in the medical device.

In a further form of embodiment, the at least one RFID transponder unit includes at least one grip area and is configured in the shape of a ball. This enables the RFID transponder unit to be held safely and comfortably in a patient's hand within the medical device and control elements, such as an initiation device, may be operated in a comfortable manner. A command is then initiated, for example, by pressing the ball-shaped RFID transponder unit also called a patient call ball or by pressing an initiation device in the form of a key.

A medical control system is also provided. In this case, the medical control system includes a control device and a medical device and is configured for transmission of at least one command according to the forms of embodiment described above.

Furthermore, an RFID transponder unit for transmission of an identification code and also a read device for reading out the identification code of the RFID transponder unit are also provided, which together form the control device in accordance with the forms of embodiment described above.

In addition, a method for transmission of at least one command between an RFID transponder unit and a read device is provided. A processor unit of the control system includes corresponding programs for executing the method.

The advantages of the medical control system, the RFID transponder unit, the read device, and the method correspond to the advantages of the control device that have previously been described in detail. Features, advantages or alternate forms of embodiment mentioned here are likewise also to be transferred to the other claimed subject matter and vice versa. In other words, the physical claims that are directed to a control device, for example, may also be further developed with the features that are described or claimed in conjunction with a method. The corresponding functional claims of the method are configured in such cases by corresponding physical modules, such as by hardware modules.

DETAILED DESCRIPTION

Figure 1:
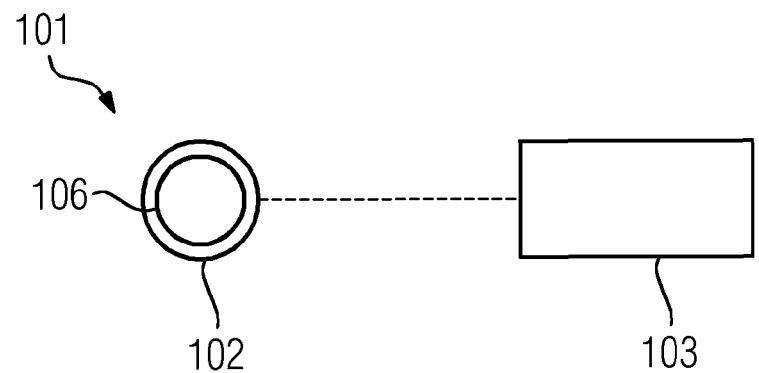
FIG. 1 depicts an embodiment of a control device.

FIG. 1 depicts a control device 101 for transmission of at least one command. The control device 101 includes an RFID transponder unit 102 for transmission of an identification code and a read device 103 for reading out the identification code of the RFID transponder unit. The RFID transponder unit 102 of the control device 101 may be disposed within a medical device 104 (see also FIG. 2) and has an initiation device 106 for initiating the at least one command. A command is to be understood, for example, as a modification of a parameter, such as the modification of the volume of music, of the volume of speech, of illumination or of ventilation, but also the triggering of an alarm, for example. The initiation device 106 is then configured to initiate the corresponding command.

The RFID transponder unit 102 contains an identification code that the read device 103 may read out. A coupling occurs through magnetic alternating fields generated by the read device 103 or through high-frequency radio waves. The initiation device 106 is, for example, a pushbutton, a key, or a knob for initiating the at least one command. The initiation device 106 may be operated manually by a user, such as by a patient. In the example depicted, the command is initiated by pressing the RFID transponder unit 102 configured in the shape of a ball such that the initiation device 106 configured as a switch is actuated.

Figure 3:
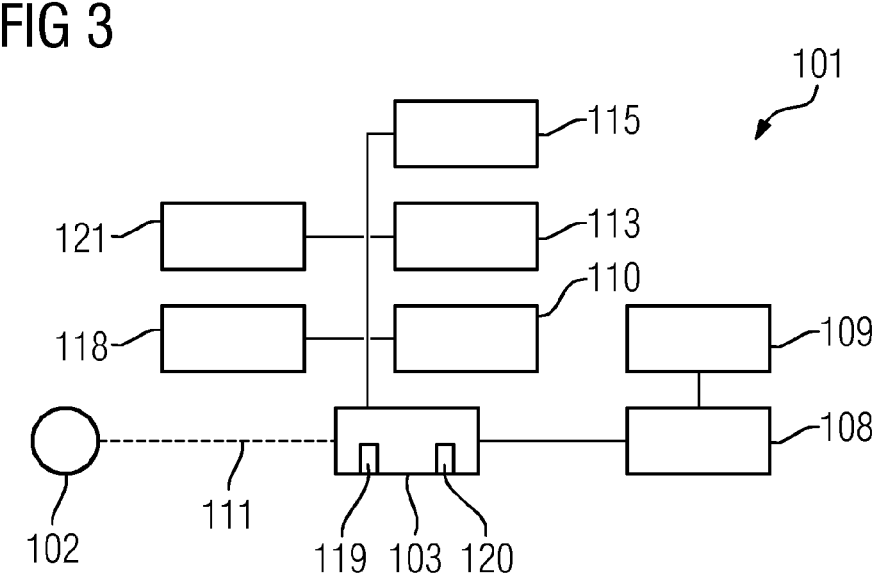
FIG. 3 depicts a further embodiment of a control device.
Figure 4:
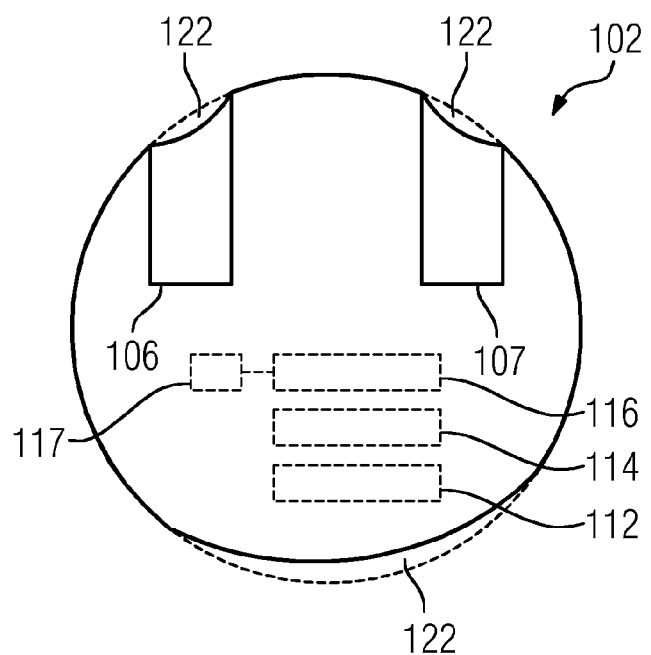
FIG. 4 depicts an embodiment of a RFID transponder unit.

The RFID transponder unit 102 of the control device 101 may also be configured, for example, in the form of the RFID transponder unit 102 from FIG. 4. The read device 103 of the control device 101 may be configured, for example, in the form of the read device 103 from FIG. 3.

Figure 2:
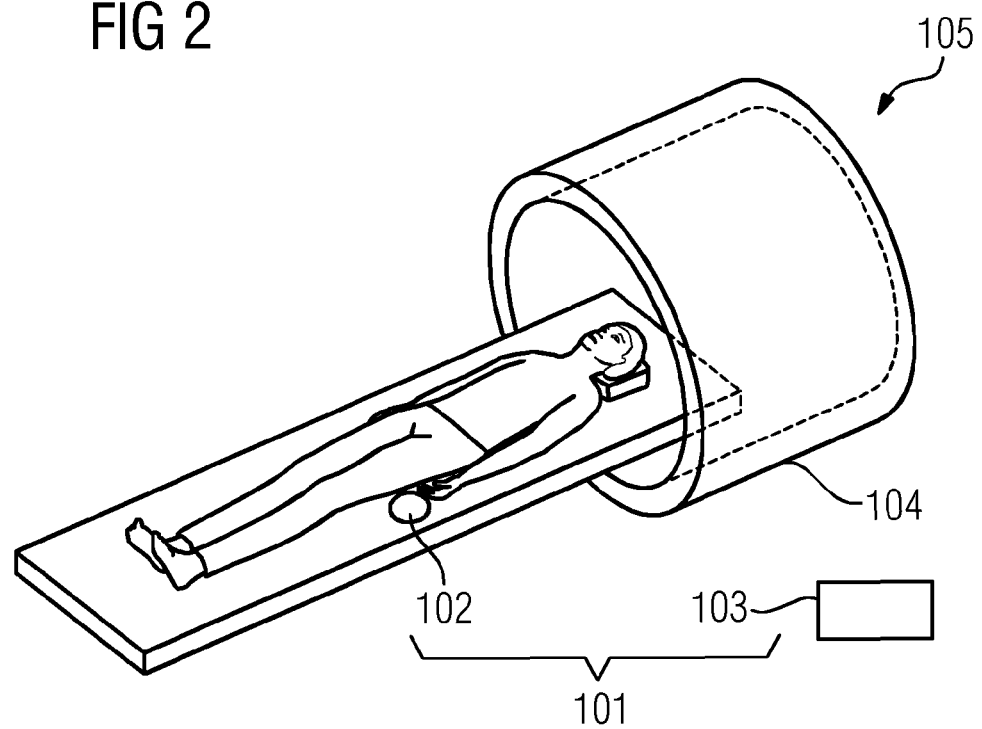
FIG. 2 depicts an embodiment of medical control system.

FIG. 2 to FIG. 4 depict further exemplary embodiments of a control device 101, a medical control system 105, or parts of a control device 101 or a medical control system 105. Components, features, and functions that remain essentially the same are basically labeled with the same reference characters. The descriptions below are restricted essentially to the differences from the exemplary embodiment in FIG. 1, whereby in relation to components, features, and functions that remain the same, the reader is referred to the description of the exemplary embodiment in FIG. 1.

FIG. 2 depicts a medical control system 105, including a control device 101 and a medical device 104. The RFID transponder unit 102 of the control device 101 is disposed within the medical device 104. It makes it possible, for example, for a patient located within the medical device 104 to initiate a command and thus to attract the attention of medical personnel.

FIG. 3 depicts a further embodiment of a control device 101. In this case, the control device 101 depicted includes a first alarm unit 108 configured for triggering a first alarm after initiation of the at least one command. A first alarm in this case is to be understood, for example, as an alarm of a patient who may trigger one of these alarms within the medical device 104. This gives the patient an opportunity of attracting attention if the patient is becoming lightheaded, for example, or wishes to make contact for other reasons.

The control device 101 is configured for switching off and/or restarting an activation mode of the first alarm. In this case, activation mode is to be understood as a mode that makes it possible to actively trigger the alarm. An alarm is to be understood, for example, as the sending of a specific command and/or data pattern. The alarm may also be realized by an illumination and/or flashing of the diode and/or by an output of an acoustic signal. Thus, by restarting the activation mode, for example, the triggering of the first alarm may be suppressed for a specific time. The embodiment for switching off the activation mode also includes switching off during the sending of a first alarm, if the alarm has been noted for example and is no longer to be transmitted. The switching off and/or restarting of the activation mode is undertaken by the medical personnel operating the control device 101.

The control device 101 further includes a user interface 109, by which the switching off and/or restarting of the activation mode of the first alarm is able to be carried out. In this case the user interface 109 may be configured as a switch, knob, or lever for example.

Furthermore, the control device 101 has a first monitoring unit 110 configured for monitoring a transmission link between the RFID transponder unit 102 and the read device 103. In this case, the first monitoring unit 110 may detect whether the transmission link is interrupted.

A second alarm unit 113 of the control device 101 is configured for triggering a second alarm if the transmission link is interrupted. Advantageously, the second alarm is triggered after interruption of the transmission link for a specific period of time. In this case, the interruption may be checked, for example, by the absence of the status message "RFID detected."

The read device 103 of the control device 101 is configured for sending on a whole-number multiple of a predeterminable basic frequency. In this case, a basic frequency is to be understood as a frequency that is predetermined by the medical device 104, for example, a frequency that corresponds to a system clock of a magnetic resonance device. By the read device 103 sending on a whole-number multiple of this predeterminable basic frequency, the medical device will not be disturbed. The read device 103 of the control device 101 may however also be configured for sending with a frequency that is larger than a predeterminable limit frequency.

A filter unit 118 of the control device 101 is configured for filtering an output signal of the read device 103. In this case, a filter unit is to be understood as a heavily-attenuating bandpass or highpass, so that measurements of a medical device, (e.g., of a medical resonance device), will not be influenced.

The read device 103 of the control device 101 includes two antennas. A higher range of the RFID transponder unit 102 is achieved by this.

A transfer unit 121 of the control device 101 is configured for transfer of the at least one command to the medical device 104 and the command may be further processed in the control device 101 and/or in the medical device 104.

The RFID transponder unit 102 of the control device 101 may also be configured in the form of the RFID transponder unit 102 from FIG. 4, for example.

FIG. 4 depicts an embodiment of a RFID transponder unit 102. In this figure, the RFID transponder unit 102 has two initiation devices 106, 107 for initiating two commands. The at least two initiation devices 106, 107, (configured as pushbuttons, keys or knobs, for example), provide further commands or parameters selectable by a patient to be transmitted.

The RFID transponder unit 102 also has a command generation unit 112 configured for transmission of a further command that is initiated independently of the initiation device 106. The transmission of the further command may include, for example, of continuously sending a status message such as "RFID detected" or a specific data pattern. This provides a transmission link between RFID transponder unit 102 and read device 103 to be monitored. The RFID transponder unit 102 is additionally configured for continuous transmission of the further command. Thus, a status message such as "RFID detected," for example, may be sent continuously at a specific time interval.

A memory unit 114 of the RFID transponder unit 102 is configured for storing the at least one initiated command. Thus, in the event of an interruption of the transmission link, the initiated command may still be stored. This command may then be signaled onwards after the restoration of a correctly functioning transmission link, and thus no information about an initiated command is lost. The RFID transponder unit 102 is configured in this case for monitoring a power supply of the RFID transponder unit 102.

An energy storage unit 116 of the RFID transponder unit 102 and a third alarm unit of the control device 101, here likewise assigned to the RFID transponder unit 102, provide that a third alarm is triggered if a charging value of the energy storage unit 116 falls below a threshold. An energy storage unit 116 is understood, for example, as a battery. The third alarm is triggered as soon as the charging value of the battery falls below the threshold, e.g., becomes smaller than a percentage of a maximum charge of the battery.

The RFID transponder unit 102 depicted is configured so that the transponder unit may be programmed. In this case, a programmable RFID transponder unit 102 is to be understood as a transponder unit with which a bidirectional data link may be set up. For example, a data link with which an acknowledgement to the RFID transponder unit 102 may be set up. Thus, a specific behavior, such as an illumination, a flashing, a vibration, or a buzzing of the RFID transponder unit may be defined by different programmed data patterns.

The RFID transponder unit 102 further includes a grip area 122 and is configured here in the shape of a ball. This enables the RFID transponder unit 102 to be held, for example, by a patient within the medical device 104 securely and comfortably in their hand and for control elements, such as initiation devices 106, 107, to be able to be operated in a convenient manner by fingers, for example. A command is then initiated, e.g., by pressing the ball-shaped RFID transponder unit 102, also referred to as a patient call ball, or by pressing an initiation devices 106, 107 in the shape of a key. The grip area 122 includes cutouts in the ball-shaped geometry of the RFID transponder unit 102 so that the surface of the hand and/or the fingers of the patient or an operator sit securely on the unit.

Instead of a programmable, active RFID transponder unit 102 use of a passive RFID transponder for sending at least two different data patterns is possible. The unit takes its energy from a field of the read device 103, and thus does not have its own energy supplies such as single-use or rechargeable battery. Monitoring of the power supply is therefore not necessary. A pushbutton is connected to the passive transponder for activation of a data pattern such as "alarm active." As soon as this pushbutton is pressed the transponder sends the alarm to the read device 103. The data pattern "RFID detected" is sent continuously by the passive transponder as soon as it is within range of the read device 103. Thus the data link is continuously monitored.

Furthermore, use of an active RFID transponder for sending at least three different data patterns is possible. As soon as the active RFID transponder comes into a field of the read device 103 and is accessed by the device, the RFID transponder begins to send. Thus, the transmission link 111 is able to be monitored easily. The active transponder is accessed, for example, at an interval of two seconds. As soon as the active transponder is accessed, the transponder sends a data pattern for "RFID detected." When a charge of a battery falls below a threshold, (e.g., below 20%), the transponder sends "low battery state." As an alternative, the active transponder may send the pattern described above independently without being accessed by the read device 103. A pushbutton is connected to the active transponder for activating the data pattern "alarm active." As soon as this pushbutton is pressed, the transponder sends the data pattern "alarm active" to the read device 103 without being interrogated by the read device 103.

As an alternative use of two passive full-duplex RFID transponders for sending a data pattern is also possible. When a number of RFID transponders are used, the RFID transponders are combined into an RFID transponder unit 102, so that, for example, a patient also simply holds an RFID transponder unit 102 in their hands. The one transponder transmits the signal "RFID detected," the other "alarm active." These transponders may obtain their energy from the fields of the read device 103, thus do not have any power supply of their own such as a single-use battery or a rechargeable battery. Thus monitoring of the power supply is unnecessary. Since for the data pattern "RFID detected" and "alarm active," two transponders independent of one another are used for realizing the data link, these are monitored separately: The passive transponders are configured to be able to be switched off. For this, an output of the RFID transponder is short-circuited with high frequency switches and/or disconnected from an antenna and this is applied to ground. A microprocessor controls the switches. For the data pattern "alarm active," manual switching on with an electric pushbutton is also possible. The microprocessor executes the following switching states for example every two seconds: 100 ms "RFID detected," 100 ms "alarm active," 100 ms "RFID detected." This pattern is evaluated on the read device 103 side as "transmission link 111 ok." The switching state "alarm active" is not interpreted as an alarm if it is 100 ms long and directly beforehand and afterwards a likewise 100 ms-long "RFID detected" is sent. If within these 300 ms a manual alarm is triggered, then this alarm is buffered and output directly afterwards.

Furthermore, the use of two passive half-duplex RFID-transponders for sending a data pattern is also possible. When a number of RFID transponders are used, the RFID transponders are combined to form a transponder unit 102, so that, for example, a patient also holds an RFID transponder unit 102 in their hands. The one RFID transponder transmits a signal "RFID detected," the other "alarm active." These transponders draw their energy from the field of the read device 103, thus do not have any power supply of their own such as a single-use battery or rechargeable battery. Thus, monitoring of the power supply is unnecessary. Since for "RFID detected" and "alarm active," two transponders independent of one another are used for realizing the data link 111, these are monitored separately: the passive transponders are configured to be able to be switched off. For this, an output of the RFID transponder is short-circuited with high frequency switches and/or disconnected from an antenna and this is applied to ground. As an alternative, an energy-storage capacitor with semiconductor switches such as photovoltaic relays or discrete transistors may be disconnected or short-circuited. A microprocessor in the RFID transponder unit 102 controls these switches. For the transponder "alarm active," manual switching on with an electrical pushbutton is also possible. The microprocessor executes the following switching states for example every two seconds: 100 ms "RFID detected," 100 ms "alarm active," 100 ms "RFID detected." This pattern is evaluated on the read device 103 side as "transmission link 111 ok." The switching state "alarm active" is not interpreted as an alarm if it is 100 ms long and directly beforehand and afterwards a likewise 100 ms-long "RFID detected" is sent. If within these 300 ms a manual alarm is triggered, then this alarm is buffered and output directly afterwards.

Finally, use of three active RFID transponders for sending a data pattern is also possible. When a number of RFID transponders are used, the RFID transponders are combined to form a transponder unit 102, so that, for example, a patient also simply holds an RFID transponder unit 102 in their hands. The first transponder transmits a signal "RFID detected," the second transmits a signal "alarm active," and the third transmits a signal "low battery state". These units take their energy from a single-use battery or a rechargeable battery. Since three independent transponders are used for "RFID detected," "alarm active," and "low battery state" to realize a transmission link 111, these units are monitored separately. The active transponders are configured so that they may be switched off by their power supply being disconnected. A microprocessor in the RFID transponder unit 102 controls these switches. For the transponder "alarm active," a manual switch-on with an electrical pushbutton is also possible. The microprocessor, for example, executes the following switching states in a two-second clock: 100 ms "RFID detected," 100 ms "alarm active," 100 ms "low battery state," 100 ms "RFID detected." This pattern is evaluated on the read device 103 side as "transmission link 111 ok." The switching states "alarm active" and "low battery state" are not interpreted as alarm or as low battery state if they last 100 ms and immediately afterwards an 100 ms-long "RFID detected" is sent. If the charge of the battery falls below a value of for example 20%, the third transponder sends a signal "low battery state." If within these 400 ms a manual alarm is triggered, this is buffered and is output directly afterwards.

A power supply for active transponders may be realized in the following manner: (1) By a single-use battery: Lithium button cells such as CR-2032 may be used here, for example. These batteries may be permanently installed in the housing of the RFID transponder unit 102 or may be replaceable. (2) By a rechargeable battery: Lithium-Ion rechargeable batteries may be used here for example. Charging cradles with charging contacts or charging cradles with contactless, inductive energy transmission may be used, for example. (3) By supercapacitors: Here too charging cradles with charging contacts or charging cradles with contactless, inductive energy transmission may be used for charging. By contrast with Lithium-Ion batteries, supercapacitors do not need any charge management and may thus easily switch from a charging state into a discharging state. Therefore, when supercapacitors are used, there is the additional option of energy harvesting. Thus electrical energy may be obtained from the field of a read device 103, from a gradient field of a magnetic resonance system, from solar cells, through piezo generators, and/or through a signal at 5 MHz, for example, emitted separately for supplying power to wireless devices. Since the voltage of a capacitor used as a power supply is not constant, this may lie above an active RFID transponder supply voltage needed and be brought to a value needed with a voltage regulator.

In summary, the embodiments relate to a control device for transmission of at least one command, including at least one RFID transponder unit for transmission of an identification code and a read device for reading out the identification code of the RFID transponder unit. The RFID transponder unit is disposed within a medical device and has at least one initiation device for initiating the at least one command. In a particular form of embodiment, the control device includes three alarm units for triggering different alarms, after initiation of the at least one command, after interruption of a transmission link, and after the charging value of an energy storage unit has fallen below a threshold.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A control device for transmission of at least one command, the control device comprising:
   at least one radio frequency identification (RFID) transponder unit for transmission of an identification code, the RFID transponder unit comprising a hand-held ball-shaped device having a plurality of initiation devices; and
   a read device for reading out the identification code of the RFID transponder unit,
   wherein one or more initiation devices of the plurality of initiation devices of the RFID transponder unit is configured to be manually operated by a patient while the patient and the RFID transponder unit are disposed within a cavity of a medical imaging device such that the medical imaging device circumferentially surrounds the patient and the RFID transponder unit within the cavity,
   wherein the RFID transponder unit is configured to initiate the at least one command while the patient and the RFID transponder unit are disposed within the cavity of the medical imaging device,
wherein the medical imaging device is a computed tomograph, a positron emission tomograph, an emission computed tomograph, or a magnetic resonance tomograph, and
wherein the control device is configured for monitoring a power supply of the RFID transponder unit.

2. The control device as claimed in claim 1, wherein the control device comprises a first alarm unit configured for initiating a first alarm after initiation of the at least one command.

3. The control device as claimed in claim 2, wherein the control device is configured for switching off, restarting, or switching off and restarting an activation mode of the first alarm.

4. The control device as claimed in claim 3, wherein the control device comprises a user interface by which the switching off, restarting, or switching off and restarting of the activation mode of the first alarm is configured to be carried out.

5. The control device as claimed in claim 1, wherein the RFID transponder unit is configured for the transmission of a further command initiated independently of the at least one command.

6. The control device as claimed in claim 5, wherein the RFID transponder unit is configured for a continuous transmission of the further command.

7. The control device as claimed in claim 1, wherein the RFID transponder unit is configured for continuous sending of the at least one command.

8. The control device as claimed in claim 1, wherein the control device is configured for monitoring a transmission link between the RFID transponder unit and the read device.

9. The control device as claimed in claim 8, wherein the control device comprises:
a first alarm unit configured to trigger a first alarm after initiation of the at least one command; and
a second alarm unit configured to trigger a second alarm in an event of an interruption of the transmission link.

10. The control device as claimed in claim 8, wherein the RFID transponder unit comprises a memory unit configured for storage of the at least one initiated command.

11. The control device as claimed in claim 1, wherein the RFID transponder unit comprises an energy storage unit, and wherein the control device comprises:
a first alarm unit configured to trigger a first alarm after initiation of the at least one command;
a second alarm unit configured to trigger a second alarm in an event of an interruption of the transmission link; and
a third alarm unit configured to trigger a third alarm if a charging value of the energy storage unit falls below a threshold.

12. The control device as claimed in claim 1, wherein the RFID transponder unit is programmable.

13. The control device as claimed in claim 1, wherein the read device is configured for sending on a whole-number multiple of a predeterminable basic frequency.

14. The control device as claimed in claim 13, wherein the control device comprises a filter unit configured for filtering an output signal of the read device.

15. The control device as claimed in claim 1, wherein the read device is configured for sending with a frequency that is greater than a predeterminable limit frequency.

16. The control device as claimed in claim 1, wherein the read device comprises at least two antennas.

17. The control device as claimed in claim 1, wherein the control device is configured for a transfer of the at least one command to the medical imaging device.

18. The control device as claimed in claim 1, wherein the at least one RFID transponder unit comprises at least one grip area.

19. A medical control system comprising:
a medical imaging device selected from a group consisting of a computed tomograph, a positron emission tomograph, an emission computed tomograph, and a magnetic resonance tomograph; and
a control device for transmission of at least one command, the control device comprising:
at least one radio frequency identification (RFID) transponder unit for transmission of an identification code, the RFID transponder unit comprising a hand-held ball-shaped device having a plurality of initiation devices; and
a read device for reading out the identification code of the RFID transponder unit,
wherein one or more initiation devices of the plurality of initiation devices of the RFID transponder unit is configured to be manually operated by a patient while the patient and the RFID transponder unit are disposed within a cavity of the medical imaging device such that the medical imaging device circumferentially surrounds the patient and the RFID transponder unit within the cavity,
wherein the RFID transponder unit is configured to initiate the at least one command while the patient and the RFID transponder unit are disposed within the cavity of the medical imaging device, and
wherein the control device is configured for monitoring a power supply of the RFID transponder unit.

20. The medical control system as claimed in claim 19, wherein the medical imaging device is the magnetic resonance tomograph.

21. The medical control system as claimed in claim 20, wherein the RFID transponder unit comprises a material configured to be compatible for examinations with the magnetic resonance tomograph.

22. A method for transmission of at least one command by a control device, the method comprising:
initiating the at least one command by a radio frequency identification (RFID) transponder unit while the RFID transponder unit is disposed within a cavity of a medical imaging device such that the medical imaging device circumferentially surrounds the patient and the RFID transponder unit within the cavity, wherein the RFID transponder unit comprises a hand-held ball-shaped device having a plurality of initiation devices and wherein the control device is configured for monitoring a power supply of the RFID transponder unit;
transmitting the command by the RFID transponder unit of the control device; and
reading out the transmitted command by a read device of the control device,
wherein the medical imaging device is a computed tomograph, a positron emission tomograph, an emission computed tomograph, or a magnetic resonance tomograph.

23. The control device as claimed in claim 1, wherein the at least one command is a modification of a volume of music, a volume of speech, illumination, or ventilation.

* * * * *